United States Patent
Hamanaga et al.

(10) Patent No.: US 11,723,551 B2
(45) Date of Patent: Aug. 15, 2023

(54) MAGNETIC RESONANCE IMAGING APPARATUS, CORRECTION METHOD, AND MEMORY MEDIUM

(71) Applicant: CANON MEDICAL SYSTEMS CORPORATION, Otawara (JP)

(72) Inventors: Shohei Hamanaga, Nasushiobara (JP); Mitsuhiro Bekku, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/503,718

(22) Filed: Oct. 18, 2021

(65) Prior Publication Data

US 2022/0133169 A1    May 5, 2022

(30) Foreign Application Priority Data

Oct. 29, 2020    (JP) ................................. 2020-181587

(51) Int. Cl.
*A61B 5/055*    (2006.01)
*G01R 33/561*    (2006.01)
*G01R 33/48*    (2006.01)

(52) U.S. Cl.
CPC .......... *A61B 5/055* (2013.01); *G01R 33/4818* (2013.01); *G01R 33/5616* (2013.01)

(58) Field of Classification Search
CPC .. G01R 33/4818; G01R 33/5616; A61B 5/055
See application file for complete search history.

(56) References Cited

U.S. PATENT DOCUMENTS

2005/0237056 A1* 10/2005 Nabetani ............ G01R 33/3415
                                                       324/309
2019/0331750 A1* 10/2019 Zhu ................... G01R 33/56341

FOREIGN PATENT DOCUMENTS

JP           2019-5136 A           1/2019

\* cited by examiner

*Primary Examiner* — Dixomara Vargas
(74) *Attorney, Agent, or Firm* — Oblon, McClelland, Maier & Neustadt, L.L.P.

(57) ABSTRACT

A magnetic resonance imaging apparatus according to an embodiment includes a processing circuitry. Regarding the k-space data obtained as a result of performing multi-shot imaging that includes a plurality of shots, the processing circuitry obtains a correction coefficient, based on first-type magnetic resonance images generated using the k-space data, the correction coefficient correcting phase shifting occurring in read out direction among the plurality of shots. Then, the processing circuitry corrects the k-space data based on the correction coefficients. Moreover, the processing circuitry generates a second-type magnetic resonance image using the corrected k-space data.

12 Claims, 9 Drawing Sheets

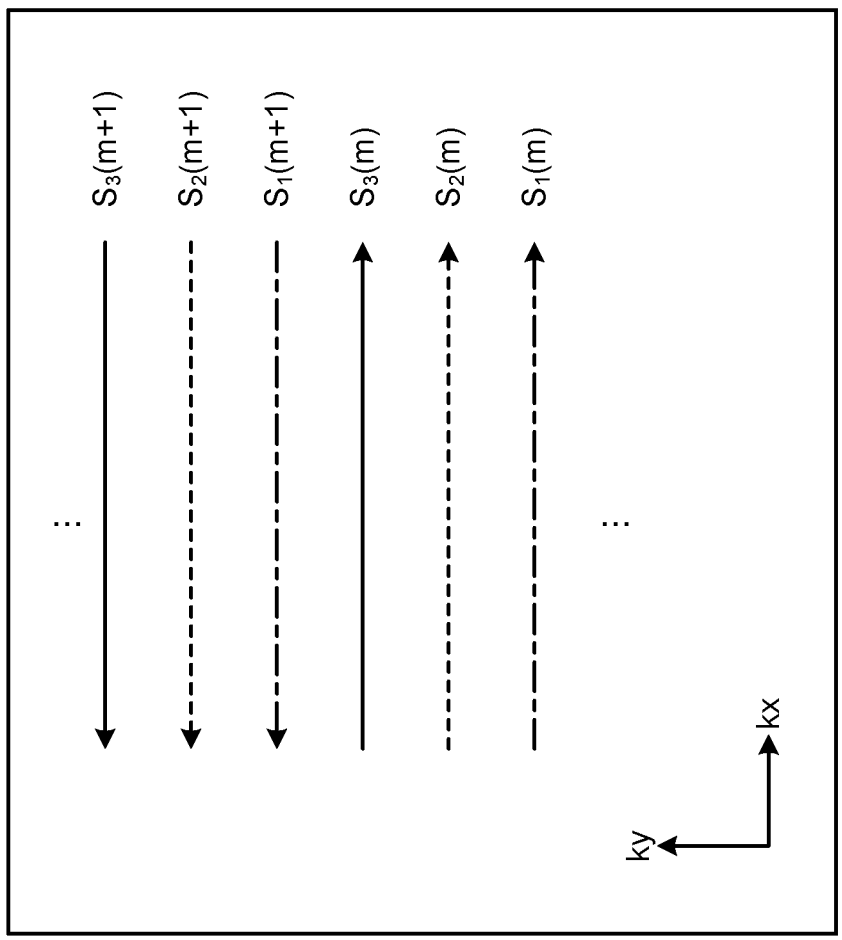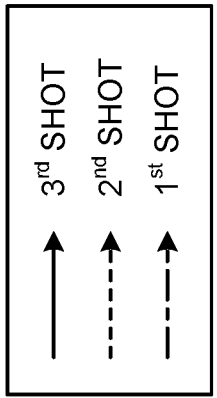

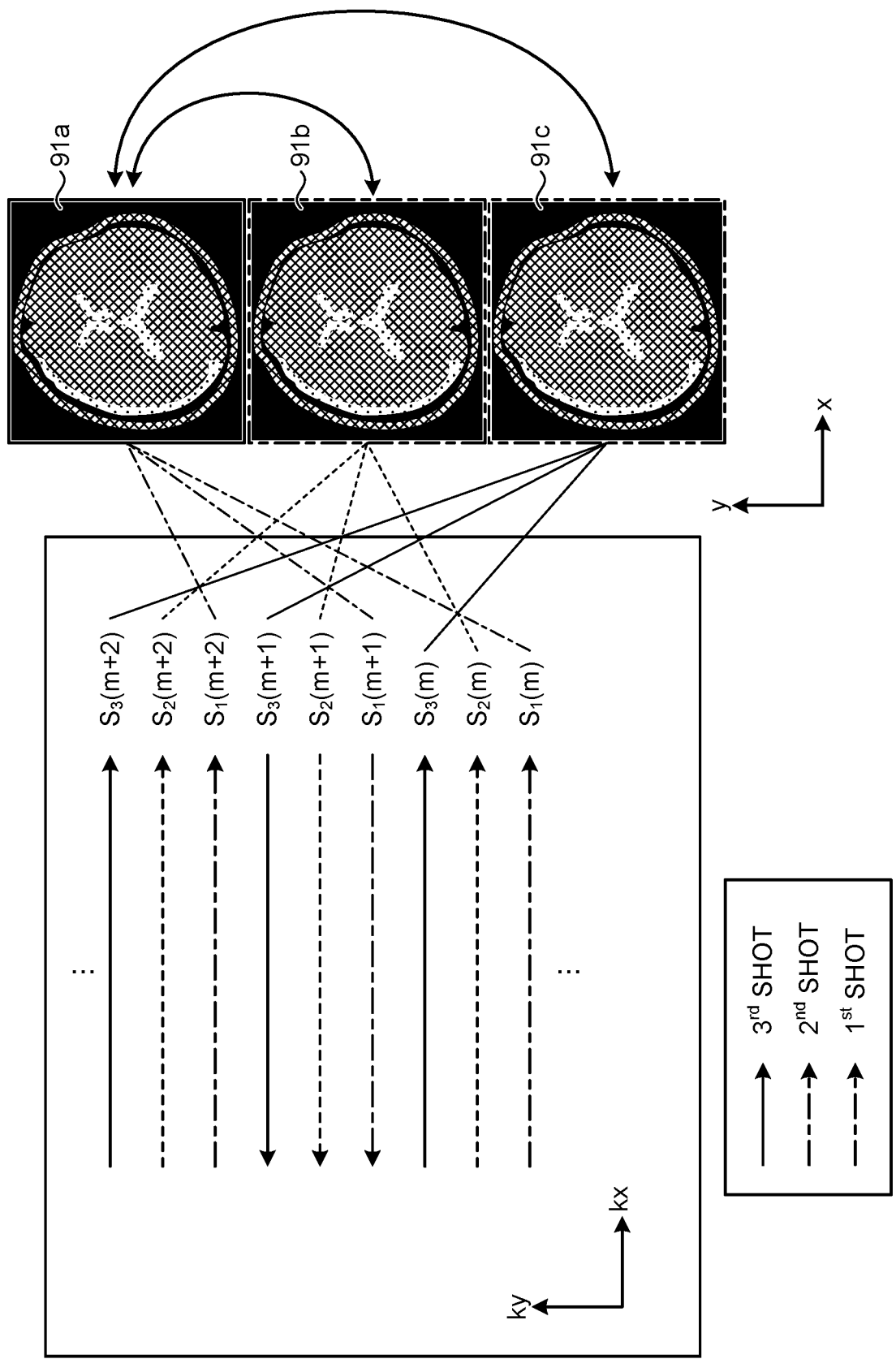

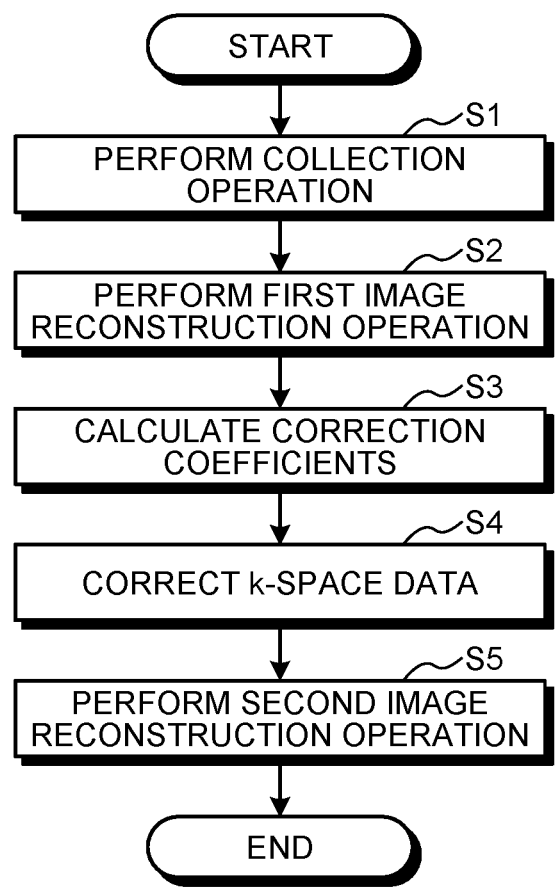

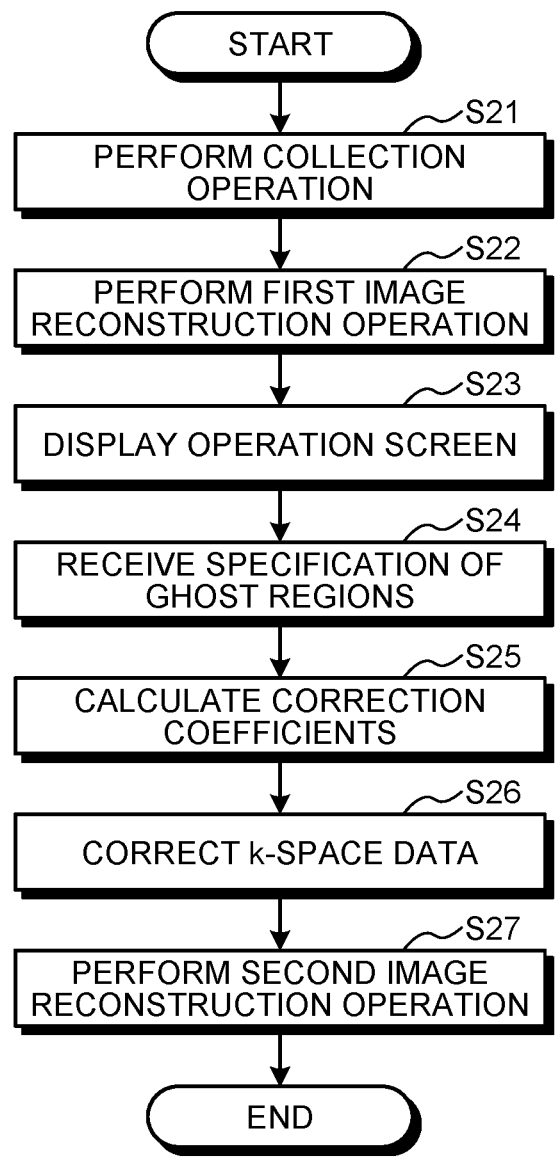

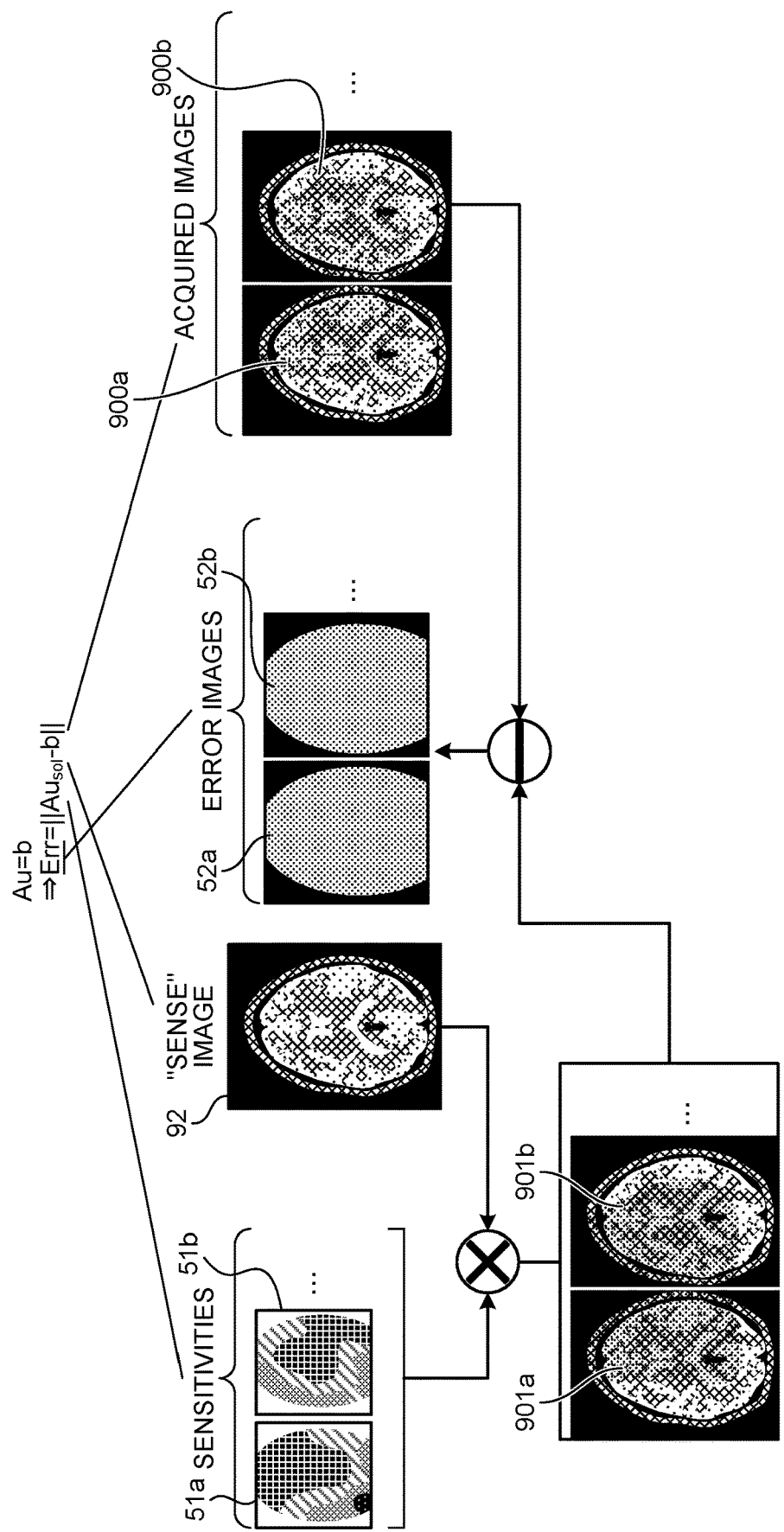

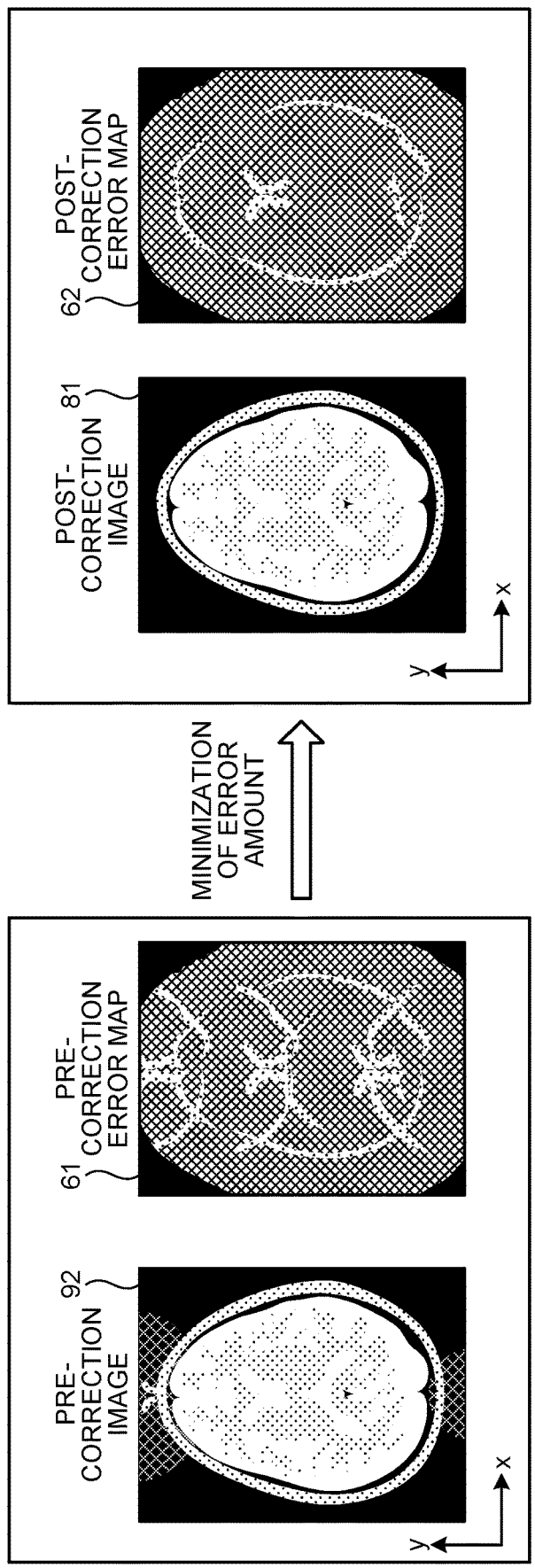

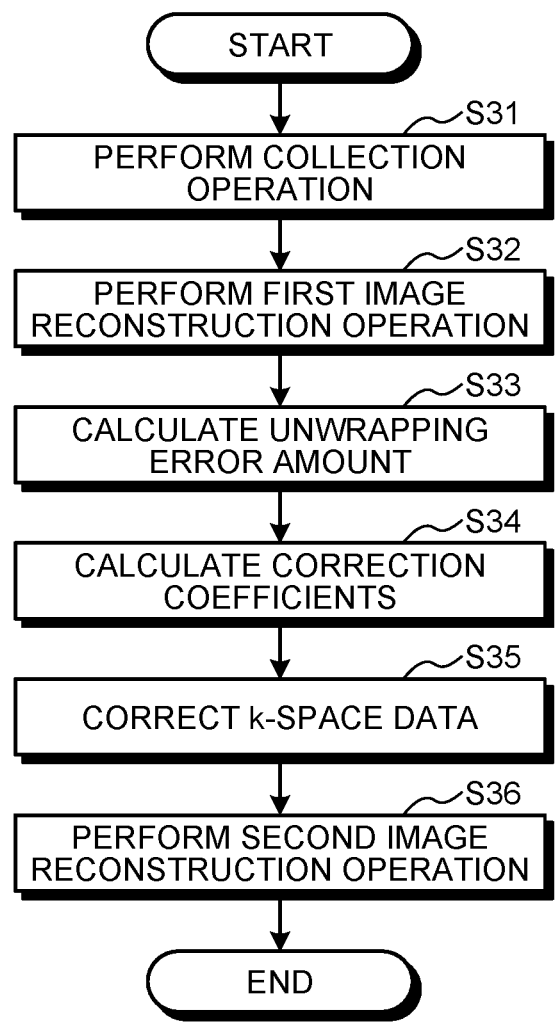

MAGNETIC RESONANCE IMAGING APPARATUS, CORRECTION METHOD, AND MEMORY MEDIUM

CROSS-REFERENCE TO RELATED APPLICATIONS

This application is based upon and claims the benefit of priority from Japanese Patent Application No. 2020-181587, filed on Oct. 29, 2020; the entire contents of which are incorporated herein by reference.

FIELD

Embodiments described herein relate generally to a magnetic resonance imaging apparatus, a correction method, and a memory medium.

BACKGROUND

Conventionally, echo planar imaging (EPI) is known as one of the imaging methods implemented using a magnetic resonance imaging (MRI) device. Moreover, EPI includes single-shot EPI and multi-shot EPI. In the single-shot EPI, k-space data equivalent to a single image is obtained at once in a single instance of excitation (in a single shot). In the multi-shot EPI, the overall k-space is filled in a phased manner across a plurality of instances of excitation. In the multi-shot EPI, high spatial resolution can be achieved by performing sampling of the overall k-space.

However, if there is phase shifting among a plurality of shots included in multi-shot imaging, there are times when an artifact occurs in the magnetic resonance images. In order to correct such phase shifting, sometimes it becomes necessary to perform complex operations. That leads to prolongation of the operations meant for imaging and reconstruction.

BRIEF DESCRIPTION OF THE DRAWINGS

FIG. 2 is a schematic diagram illustrating an example of the relationship among the echo signals obtained using multi-shot imaging according to the first embodiment;

FIG. 3 is a diagram illustrating an example of a plurality of pre-correction images corresponding to a plurality of shots according to the first embodiment;

FIG. 4 is a flowchart for explaining an exemplary flow of a correction operation according to the first embodiment;

FIG. 6 is a flowchart for explaining an exemplary flow of a correction operation according to the second embodiment;

FIG. 7 is a diagram simulatedly illustrating an example of the concept of calculation of the error according to the third embodiment;

FIG. 8 is a diagram illustrating an example of a post-correction magnetic resonance image and a post-correction error map according to the third embodiment; and FIG. 9 is a flowchart for explaining an exemplary flow of a correction operation according to the third embodiment.

DETAILED DESCRIPTION

Exemplary embodiments of a magnetic resonance imaging apparatus, a correction method, and a memory medium are described below in detail with reference to the accompanying drawings.

First Embodiment

A magnetic resonance imaging apparatus according to an embodiment includes a processing circuitry. Regarding the k-space data obtained as a result of performing multi-shot imaging that includes a plurality of shots, the processing circuitry obtains a correction coefficient, based on first-type magnetic resonance images generated using the k-space data, the correction coefficient correcting phase shifting occurring in read out direction among the plurality of shots. Then, the processing circuitry corrects the k-space data based on the correction coefficients. Moreover, the processing circuitry generates a second-type magnetic resonance image using the corrected k-space data.

Figure 1:
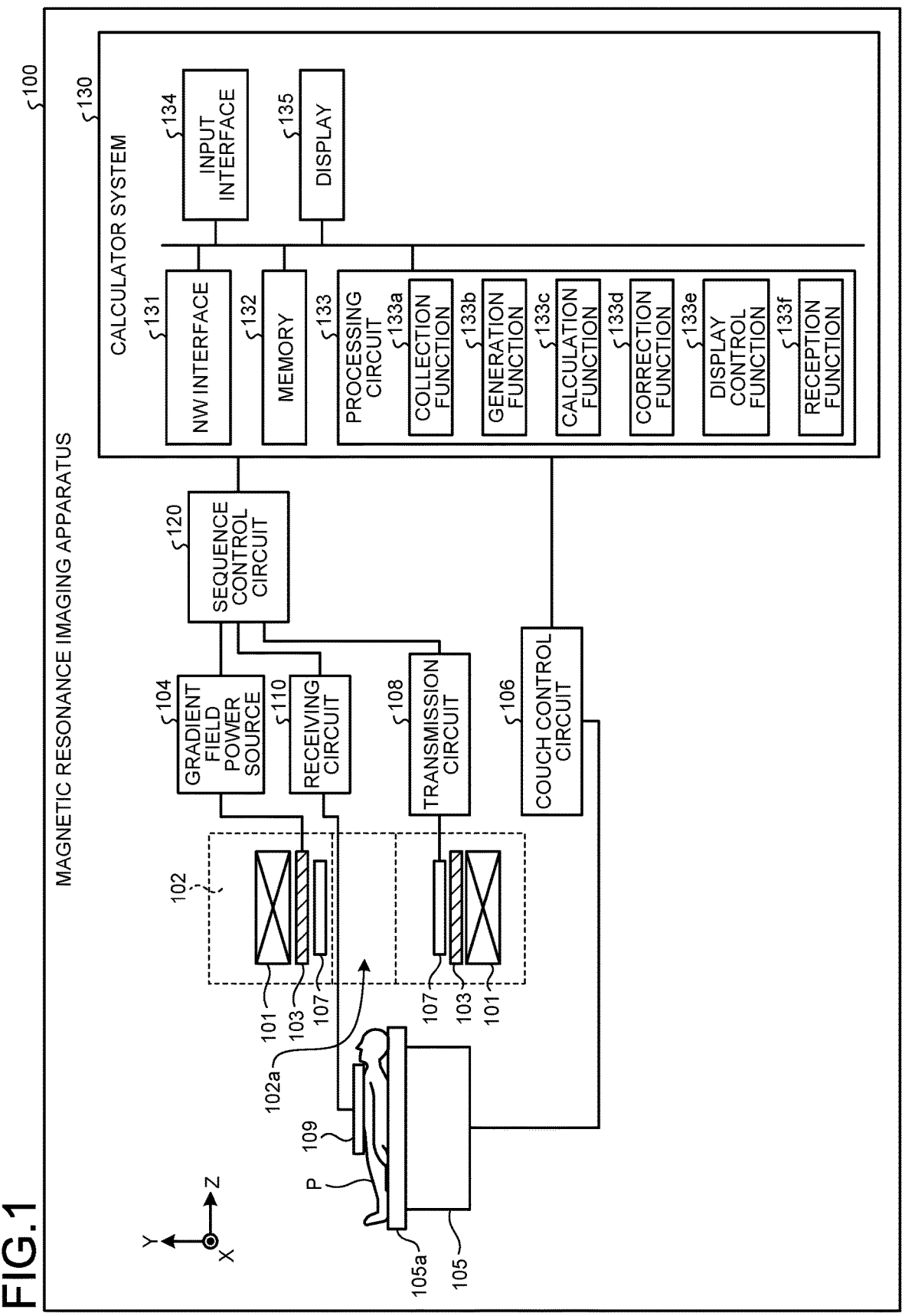
FIG. 1 is a block diagram illustrating an example of a magnetic resonance imaging apparatus according to a first embodiment.

FIG. 1 is a block diagram illustrating an example of a magnetic resonance imaging (MRI) device 100 according to a first embodiment. As illustrated in FIG. 1, the magnetic resonance imaging apparatus 100 includes a magnetostatic magnet 101, a mount 102, a magnetostatic field power source (not illustrated), a gradient coil 103, a gradient field power source 104, a couch 105, a couch control circuit 106, a whole-body radio frequency (RF) coil 107, a transmission circuit 108, a topical RF coil 109, a receiving circuit 110, a sequence control circuit 120, and a calculator system 130.

The configuration illustrated in FIG. 1 is only exemplary. Alternatively, for example, the constituent elements of the sequence control circuit 120 and the calculator system 130 can be appropriately integrated or separated. Moreover, the magnetic resonance imaging apparatus 100 can include some other configurations too. Meanwhile, a subject P (for example, a human being) is not a part of the magnetic resonance imaging apparatus 100.

The X-axis, the Y-axis, and the Z-axis illustrated in FIG. 1 constitute the device coordinate system specific to the magnetic resonance imaging apparatus 100. For example, the Z-axis direction is coincident with the axial direction of the cylinder hollow of the gradient coil 103, and is set to run along the magnetic flux of the electrostatic magnetic field generated due to the magnetostatic magnet 101. Moreover, the Z-axis direction is aligned in the same direction as the longitudinal direction of the couch 105 and in the same direction as the craniocaudal direction of the subject P who is asked to lie down on the couch 105. The X-axis direction is set along the horizontal direction that is orthogonal to the Z-axis direction. The Y-axis direction is set along the vertical direction that is orthogonal to the Z-axis direction.

The magnetostatic magnet 101 is a hollow magnet having a substantially cylindrical shape, and generates a magnetostatic field in its internal space. The magnetostatic magnet 101 is, for example, a superconducting magnet that receives the supply of an electric current from the magnetostatic field power source and becomes energized. Thus, the magnetostatic field power source supplies an electric current to the magnetostatic magnet 101. As another example, the magnetostatic magnet 101 can be a permanent magnet. In that case, the magnetic resonance imaging apparatus 100 need not include the magnetostatic field power source. Meanwhile, it is also possible to have the magnetostatic field power source installed separately from the magnetic resonance imaging apparatus 100.

The mount 102 has a hollow bore 102a formed in a substantially cylindrical shape; and has the magnetostatic magnet 101, the gradient coil 103, and the whole-body RF coil 107 housed therein. More particularly, in the mount 102, the whole-body RF coil 107 is disposed on the outer periphery side of the bore 102a; the gradient coil 103 is disposed on the outer periphery side of the whole-body RF coil 107; and the magnetostatic magnet 101 is disposed on the outer periphery side of the gradient coil 103. The space inside the bore 102a of the mount 102 serves as the imaging space into which the subject P is positioned during imaging.

Meanwhile, in the first embodiment, the term "circle" also covers the meaning of "ellipse". Moreover, in the first embodiment, the term "cylindrical shape" is not limited to imply that the cross-sectional shape orthogonal to the central axis of a cylinder is exactly circular. Thus, the term "cylindrical shape" also includes the case in which the cross-sectional shape orthogonal to the central axis of a cylinder is elliptical.

The gradient coil 103 is a hollow coil having a substantially cylindrical shape, and is disposed on the inside of the magnetostatic magnet 101. The gradient coil 103 is formed by combining three coils corresponding to the X, Y, and Z axes that are mutually orthogonal; and those three coils individually receive the supply of an electric current from the gradient field power source 104 and generate gradient fields in which the magnetic field intensity changes along the X, Y, and Z axes, respectively. The gradient field power source 104 supplies an electric current to the gradient coil 103 under the control of the sequence control circuit 120.

The couch 105 includes a couchtop 105a on which the subject P is asked to lie down. Under the control of the couch control circuit 106; the couchtop 105a, on which the subject P such as a patient is lying down, is inserted in the imaging opening. Under the control of the calculator system 130, the couch control circuit 106 drives the couch 105 and moves the couchtop 105a in the longitudinal direction and the vertical direction.

The whole-body RF coil 107 is a coil of the whole-body type that surrounds the whole body of the patient P. The whole-body RF coil 107 is disposed on the inner periphery side of the gradient coil 103; and applies an RF magnetic field onto the patient P positioned in the imaging space and receives magnetic resonance signals coming from the subject P due to the impact of the RF magnetic field. More particularly, the whole-body RF coil 107 is a hollow coil having a substantially cylindrical shape; and, based on the RF pulses supplied from the transmission circuit 108, applies an RF magnetic field onto the subject P who is positioned in the imaging space formed on the inner periphery side of the whole-body RF coil 107. Moreover, the whole-body RF coil 107 receives magnetic resonance signals (MR signals) coming from the subject P due to the impact of the RF magnetic field, and outputs the magnetic resonance signals to the receiving circuit 110.

The topical RF coil 109 receives the magnetic resonance signals coming from the subject P. More particularly, the topical RF coil 109 caters to each body part of the subject P and, during the imaging of the subject P, is disposed close to the target body part for imaging. Then, the topical RF coil 109 receives the magnetic resonance signals coming from the subject P due to the impact of the RF magnetic field applied by the whole-body RF coil 107, and outputs the magnetic resonance signals to the receiving circuit 110.

The topical RF coil 109 is, for example, a phased array coil configured by combining a plurality of surface coils serving as coil elements. The surface coils included in the topical RF coil 109 represent an example of a plurality of coils according to the first embodiment.

The topical RF coil 109 can also have the functionality of a transmission coil that applies an RF magnetic field onto the subject P. In that case, the topical RF coil 109 is connected to the transmission circuit 108, and applies an RF magnetic field onto the subject P based on the RF pulse signals supplied from the transmission circuit 108.

The transmission circuit 108 supplies RF pulses to the whole-body RF coil 107 under the control of the sequence control circuit 120.

The receiving circuit 110 performs analog-to-digital (AD) conversion of the analog MR signals output from the whole-body RF coil 107 or the topical RF coil 109; and generates MR data. Moreover, the receiving circuit 110 sends the MR data to the sequence control circuit 120. Meanwhile, AD conversion can be alternatively performed in the whole-body RF coil 107 or the topical RF coil 109. Moreover, the receiving circuit 110 is also capable of performing arbitrary signal processing other than AD conversion.

The sequence control circuit 120 drives the gradient field power source 104, the transmission circuit 108, and the receiving circuit 110 based on the sequence information sent from the calculator system 130; and performs imaging of the subject P.

Herein, sequence information represents information in which the sequence for performing the imaging is defined. In the sequence information, the following information is defined: the intensity and the supply timing of the electric current supplied from the gradient field power source 104 to the gradient coil 103; the intensity and the application timing of the RF pulses supplied from the transmission circuit 108 to the whole-body RF coil 107; and the timing of detection of the MR signals by the receiving circuit 110. However, the sequence information differs according to the range of the target region for imaging in the body of the subject P.

The sequence control circuit 120 can be implemented using a processor, or can be implemented using a combination of software and hardware.

As a result of performing imaging of the subject P by driving the sequence control circuit 120, the gradient field power source 104, the transmission circuit 108, and the receiving circuit 110; the sequence control circuit 120 receives MR data from the receiving circuit 110 and transfers it to the calculator system 130.

The calculator system 130 performs overall control of the magnetic resonance imaging apparatus 100, and generates MR images. As illustrated in FIG. 1, the calculator system 130 includes a network (NW) interface 131, a memory 132, a processing circuit 133, an input interface 134, and a display 135.

The NW interface 131 performs communication with the sequence control circuit 120 and the couch control circuit 106. For example, the NW interface 131 sends the sequence information to the sequence control circuit 120. Moreover, the NW interface 131 receives the MR data from the sequence control circuit 120.

The memory 132 is used to store the following: the MR data received by the NW interface 131; k-space data placed in the k-space by the processing circuit 133 (explained later); and image data generated by the processing circuit 133. The memory 132 is, for example, a semiconductor memory device such as a random access memory (RAM) or a flash memory; or a hard disk; or an optical disk. Meanwhile, the memory 132 can alternatively be stored on the outside of the magnetic resonance imaging apparatus 100.

The input interface 134 receives input of various instructions or information from the operator. The input interface 134 is, for example, a trackball; switch buttons; a mouse; a keyboard; a touchpad that enables performing an input operation by touching an operation screen; a touch-sensitive screen in which a display screen and a touchpad are integrated; a contactless input circuit in which an optical sensor is used; or a voice input circuit. The input interface is connected to the processing circuit 133; and converts the input operation received from the operator into electrical signals and outputs the electrical signals to the processing circuit 133. Meanwhile, in the present written description, the input interface is not limited to include a physical operating component such as a mouse or a keyboard. For example, as an example of the input interface, it is possible to use an electrical signal processing circuit that receives electrical signals corresponding to an input operation from an external input device installed separately from the calculator system 130, and that outputs the electrical signals to the control circuit.

The display 135 displays the following under the control of the processing circuit 133: a graphical user interface (GUI) meant for receiving input of imaging conditions; and magnetic resonance images generated by the processing circuit 133. The display 135 is, for example, a display device such as a liquid crystal display. Herein, the display 135 represents an example of a display unit. Meanwhile, the display 135 can alternatively be installed on the outside of the magnetic resonance imaging apparatus 100.

The processing circuit 133 performs overall control of the magnetic resonance imaging apparatus 100. More specifically, as an example, the processing circuit 133 includes a collection function 133a, a generation function 133b, a calculation function 133c, a correction function 133d, a display control function 133e, and a reception function 133f. The collection function 133a represents an example of a collecting unit. The generation function 133b represents an example of a generating unit. The calculation function 133c represents an example of a calculating unit and an obtaining unit. The correction function 133d represents an example of a correcting unit. The display control function 133e represents an example of a display control unit. The reception function 133f represents an example of a receiving unit.

For example, the processing functions representing the constituent elements of the processing circuit 133, such as the collection function 133a, the generation function 133b, the calculation function 133c, the correction function 133d, the display control function 133e, and the reception function 133f are stored in the form of computer-executable programs in the memory 132. In other words, after having read those computer programs, the processing circuit 133 gets equipped with the functions illustrated in the processing circuit 133 in FIG. 1. Meanwhile, with reference to FIG. 1, the processing functions such as the collection function 133a, the generation function 133b, the calculation function 133c, the correction function 133d, the display control function 133e, and the reception function 133f are implemented in a single processor. However, alternatively, the processing circuit 133 can be configured by combining a plurality of independent processors, and each processor can execute computer programs and implement the functions. Moreover, with reference to FIG. 1, the computer programs corresponding to the processing functions are stored in a single memory 132. However, alternatively, a plurality of memory can be disposed in a dispersed manner, and the processing circuit can read computer programs from individual memory.

The collection function 133a and the generation function 133b according to the first embodiment perform an imaging operation for taking magnetic resonance images according to parallel imaging (PI) in which the imaging time is shortened using the differences in sensitivity of the coils included in the topical RF coil 109.

More specifically, the collection function 133a executes various pulse sequences and collects MR data, which is obtained by conversion of MR signals coming from the subject P, from the sequence control circuit 120 via the NW interface 131. Moreover, the collection function 133a places the collected MR data in the k-space according to the phase encoding amount or the frequency encoding amount assigned because of the gradient field.

The MR data placed in the k-space is referred to as k-space data. The k-space data is stored in the memory 132. The coordinates in the k-space data are expressed using a kx-axis, a ky-axis, and a k-axis. In the k-space, the kx-axis and the ky-axis correspond to the horizontal axis (the x-axis) and the vertical axis (the y-axis) of a two-dimensional (2D) image. The k-axis does not represent positions in the real space, but represents spatial frequencies in the x-direction and the y-direction.

Thus, as explained above, the k-space data according to the first embodiment represents data obtained using the topical RF coil 109 that includes a plurality of coils.

The collection function 133a according to the first embodiment implements multi-shot echo planar imaging (EPI) and collects echo signals in the read out direction of a plurality of lines due to excitation on multiple occasions. The echo signals are one of types of MR signals.

FIG. 2 is a schematic diagram illustrating an example of the relationship among the echo signals obtained using multi-shot imaging according to the first embodiment. More particularly, the multi-shot imaging includes a 1-st shot, a 2-nd shot, and a 3-rd shot. During each shot, a plurality of echo signals are collected. With reference to FIG. 2, "the m-th echo signal of the n-th shot" is expressed as $S_n(m)$. For example, $S_1(1)$ represents the first echo signal of the 1-st shot. Similarly, $S_2(1)$ represents the first echo signal of the 2-nd shot. The 1-st shot represents an example of a first shot according to the first embodiment. The 2-nd shot represents an example of a second shot according to the first embodiment. The 3-rd shot represents an example of a third shot according to the first embodiment.

With reference to FIG. 2, the explanation is given for an example in which a total of three shots are included in the multi-shot imaging. However, the number of shots is not limited to that example. That is, as long as the multi-shot imaging includes two or more shots, it serves the purpose.

The kx-axis direction illustrated in FIG. 2 indicates the read out direction in the k-space. Moreover, the ky-axis illustrated in FIG. 2 indicates the ky-coordinates in the case in which the echo signals are converted into k-space data and filled in the k-space.

Generally, in a plurality of echo signals obtained as a result of performing multi-shot imaging, there occurs phase shifting in the read out direction among a plurality of shots included in the multi-shot imaging. The phase shifting in the read out direction includes phase shifting of a plurality of arbitrary degrees. For example, the phase shifting in the read out direction includes the 0-degree phase shifting. Meanwhile, in the first embodiment, from among the phase shifting in the read out direction, the explanation is particularly given about the 0-degree phase shifting and the 1-degree phase shifting.

The phase shifting implies, for example, the shifting of the peak positions in the read out direction of a plurality of echo signals collected as a result of taking a plurality of shots. The phase shifting occurs because of, for example, the hardware-specific device characteristics of each magnetic resonance imaging apparatus 100 or because of the incompleteness of the sequence design. However, those are not the only possible reasons.

When there occurs phase shifting in the read out direction among a plurality of shots, the relationship between the echo signals obtained in the 1-st shot and the echo signals obtained in the n-th shot can be modeled as given below in Equation (1).

$$\text{Phase error between 1-st shot and } n\text{-th shot} = c_{n,k} x^k + c_{n,k-1} x^{k-1} + \ldots + c_{n,1} x + c_{n,0} \quad (1)$$

In Equation (1), the phase shifting among the shots in the read out direction in the real space is modeled as a polynomial equation. Moreover, in Equation (1), k represents the degree of the polynomial equation.

Because of such phase shifting, sometimes there occurs an artifact in the magnetic resonance images formed based on the k-space data that is obtained by conversion of the echo signals. Thus, correction coefficients meant for correcting such phase shifting are calculated by the calculation function 133c (explained later). Meanwhile, the phase shifting among a plurality of shots sometimes includes phase shifting of a high degree. However, in the first embodiment, the explanation is given for the case in which the degree k in Equation (1) is equal to "1", that is, the case in which the 0-degree phase shifting and the 1-degree phase shifting is treated as the correction target.

Returning to the explanation with reference to FIG. 1, the generation function 133b generates magnetic resonance images based on the k-space data stored in the memory 132. For example, the generation function 133b performs a reconstruction operation such as Fourier transform with respect to the k-space data, and generates magnetic resonance images. Then, the generation function 133b stores the magnetic resonance images in, for example, the memory 132.

More specifically, the generation function 133b according to the first embodiment generates folded-over images by reconstructing the k-space data that is based on the MR data obtained using the topical RF coil 109; unwraps the folded-over images using sensitivity encoding (SENSE); and generates magnetic images. Alternatively, it is also possible to implement some other parallel imaging technique such as simultaneous acquisition of spatial harmonic (SMASH) or generalized autocalibrating partially parallel acquisitions (GRAPPA).

Firstly, based on the pre-correction k-space data, the generation function 133b generates a plurality of magnetic resonance images corresponding to a plurality of shots included in multi-shot imaging. In the following explanation, such magnetic resonance images are called pre-correction images. Moreover, such magnetic resonance images represent an example of first-type magnetic resonance images according to the first embodiment.

FIG. 3 is a diagram illustrating an example of a plurality of pre-correction images 91a to 91c corresponding to a plurality of shots according to the first embodiment. The pre-correction image 91a corresponds to the echo signals obtained in the 1-st shot. More specifically, the generation function 133b performs a reconstruction operation with respect to the k-space data obtained by conversion of the echo signals that are obtained in the 1-st shot, and generates the pre-correction image 91a. Similarly, the pre-correction image 91b corresponds to the echo signals obtained in the 2-nd shot. Moreover, the pre-correction image 91c corresponds to the echo signals obtained in the 3-rd shot. In the following explanation, in the case of not particularly distinguishing among the pre-correction images 91a to 91c, they are simply referred to as pre-correction images 91.

The pre-correction image 91a represents an example of a first image according to the first embodiment. The pre-correction image 91b represents an example of a second image according to the first embodiment. The pre-correction image 91c represents an example of a third image according to the first embodiment.

In FIG. 3, the coordinates of the k-space data, which is based on the echo signals collected in a plurality of shots, are simulatedly illustrated in the kx-axis and the ky-axis. The kx-axis represents the read out (RO) axis, and the ky-axis represents the phase encode (PE) axis. Meanwhile, in the pre-correction images, the horizontal direction corresponds to the x-axis of the real space, and the vertical direction corresponds to the y-axis of the real space.

The generation function 133b also generates a magnetic resonance image using the k-space data corrected by the correction function 133d (explained later). In the following explanation, such a magnetic resonance image is referred to as a post-correction image. Moreover, such a magnetic resonance image represents an example of a second-type magnetic resonance image according to the first embodiment. For example, from the corrected k-space data, the generation function 133b generates a single post-correction image. In the post-correction image, the artifact attributed to the phase shifting in the read out direction is lower as compared to the pre-correction images.

Returning to the explanation with reference to FIG. 1, the calculation function 133c obtains the correction coefficients based on the pre-correction images 91 generated using the k-space data.

The correction coefficients are meant for correcting, in regard to the k-space data obtained due to multi-shot imaging that includes a plurality of shots, the phase shifting occurring in the read out direction among the plurality of shots.

In the first embodiment, simply the term "obtain" implies "obtain by calculation" as well as "receive from outside". In a more limited sense, the calculation function 133c calculates the correction coefficients based on the pre-correction images 91. That is, the calculation function 133c according to the first embodiment obtains the correction coefficients by calculation.

Returning to the explanation with reference to FIG. 3, the following explanation is given about the method for calculating the correction coefficients. The calculation function 133c obtains the correction coefficients based on the correlation of comparison images with a reference image. The reference image represents one a plurality of pre-correction images 91. The comparison images represent the other pre-correction images 91 other than the reference image from among a plurality of pre-correction images 91.

In the example illustrated in FIG. 3, the pre-correction image 91a represents the reference image; and the pre-correction images 91b and 91c represent the comparison images.

Firstly, based on the pre-correction images 91a and 91b, the calculation function 133c obtains a first-type correction coefficient with respect to the pre-correction image 91*b*. The first-type correction coefficient is meant for correcting the phase shifting between the 1-st shot and 2-nd shot. As given earlier in Equation (1), in the first embodiment, the first-type correction coefficient indicates the amount of phase shifting between the 0-degree and the 1-degree.

For example, the calculation function 133*c* obtains the first-type correction coefficient by solving the optimization problem in such a way that coefficient of correlation between the pre-correction images 91*a* and 91*b* reaches the maximum value. In order to solve the optimization problem, any known method can be implemented.

Moreover, in each of the pre-correction images 91*a* and 91*b*, the calculation function 133*c* can perform a mask operation based on the corresponding signal intensity and the corresponding phase dispersion; and can obtain the coefficient of correlation between the images subjected to the mask operation. For example, regarding the positions having low signal intensity or the positions having a sharp change in the phase, there is a high likelihood of disturbance at such positions. For that reason, the calculation function 133*c* can perform the mask operation so as to exclude the positions at which there is a high likelihood of disturbance; so that those positions need not be taken into account in the calculation of the coefficient of correlation.

Moreover, based on the pre-correction images 91*a* and 91*c*, the calculation function 133*c* obtains a second-type correction coefficient with respect to the pre-correction image 91*c*. The method for calculating the second-type correction coefficient is identical to the method for calculating the first-type correction coefficient. In the calculation method according to the first embodiment, the number of comparisons among the pre-correction images 91 increases in proportion to the number of shots included in multi-shot imaging. Moreover, since a correction coefficient that is meant for correcting the phase shifting between two pre-correction images 91 is to be obtained in each instance of comparison, the count of the unknown numbers getting calculated in each instance of comparison of two pre-correction images 91 remains the same regardless of the number of shots included in multi-shot imaging.

Returning to the explanation with reference to FIG. 1, the correction function 133*d* corrects the k-space data based on the correction coefficients calculated by the calculation function 133*c*. For example, in the example explained with reference to FIG. 3, the correction function 133*d* corrects the k-space data based on the first-type correction coefficient and the second-type correction coefficient.

The first-type correction coefficient and the second-type correction coefficient are calculated based on the pre-correction images 91 in the real space that is expressed using the x-axis and y-axis. Hence, for example, with respect to projection data of each echo as obtained by performing inverse Fourier transform in the read out direction with respect to the k-space data, the correction function 133*d* corrects the phase shifting in the real space using the first-type correction coefficient and the second-type correction coefficient, and then performs Fourier transform in the read out direction with respect to the post-correction projection data of each echo. With that, the correction function 133*d* corrects the phase shifting of the k-space data.

For example, using the first-type correction coefficient calculated by the calculation function 133*c*, the correction function 133*d* corrects the phase shifting of the k-space data corresponding to the echo signals obtained in the 2-nd shot. Moreover, using the second-type correction coefficient calculated by the calculation function 133*c*, the correction function 133*d* corrects the k-space data corresponding to the echo signals obtained in the 3-rd shot. That results in correction of the phase shifting of the 2-nd shot and the 3-rd shot with respect to the 1-st shot.

In the first embodiment, the 1-st shot is treated as the reference and the k-space data corresponding to the 2-nd shot and the 3-rd shot is treated as the correction target. However, alternatively, some other shot other than the 1-st shot can be treated as the reference.

Returning to the explanation with reference to FIG. 1, the display control function 133*e* displays various types of images and a GUI in the display 135. For example, the display control function 133*e* displays the pre-correction images 91 and the post-correction image in the display 135.

The reception function 133*f* receives various types of operations from the user via the input interface 134.

Given below is the explanation of the flow of the correction operation performed in the magnetic resonance imaging apparatus 100 configured as explained above according to the first embodiment.

FIG. 4 is a flowchart for explaining an exemplary flow of the correction operation according to the first embodiment.

Firstly, the collection function 133*a* performs multi-shot EPI and collects echo signals in the read out direction of a plurality of lines (S1). Then, the collection function 133*a* generates k-space data by placing MR data, which is obtained by conversion of the collected echo signals, in the k-space data according to the phase encoding amount or the frequency encoding amount assigned because of the gradient field.

Subsequently, the generation function 133*b* performs a reconstruction operation such as Fourier transform with respect to the k-space data and performs an unwrapping operation using SENSE, and generates the pre-correction images 91*a* to 91*c* corresponding to a plurality of shots. In the first embodiment, this operation is called a first image reconstruction operation (S2).

Then, based on the pre-correction images 91*a* to 91*c*, the calculation function 133*c* calculates correction coefficients (S3). More specifically, based on the pre-correction images 91*a* and 91*b*, the calculation function 133*c* obtains the first-type correction coefficient. Moreover, based on the pre-correction images 91*a* and 91*c*, the calculation function 133*c* obtains the second-type correction coefficient.

Subsequently, based on the first-type correction coefficient and the second-type correction coefficient, the correction function 133*d* corrects the k-space data (S4).

Then, the generation function 133*b* generates a post-correction image using the corrected k-space data. This operation is called a second image reconstruction operation (S5). That marks the end of the operations illustrated in the flowchart.

In this way, in the magnetic resonance imaging apparatus 100 according to the first embodiment, the correction coefficients that are meant for correcting the phase shifting occurring in the read out direction among a plurality of shots of the k-space data, which is obtained as a result of performing multi-shot imaging including a plurality of shots, are obtained based on the pre-correction images 91 that represent real-space images generated using the k-space data. Then, in the magnetic resonance imaging apparatus 100 according to the first embodiment, the k-space data is corrected based on the obtained correction coefficients, and a post-correction image is generated using the corrected k-space data.

Conventionally, as a method for correcting the phase shifting among a plurality of shots, a method is known in which the frequency encoding direction and the read out direction are corrected in a simultaneous manner. Such a method is used in correcting, for example, the phase shifting occurring in multi-shot imaging of a diffusion weighted MRI (DWI), but sometimes there is an increase in the processing load and the processing time of the correction operation. However, in multi-shot EPI, there are times when the correction of the frequency encoding direction is not important as far as enhancing the image quality of the magnetic resonance images is concerned.

In contrast, in the magnetic resonance imaging apparatus 100 according to the first embodiment, as a result of obtaining the correction coefficients that are meant for correcting the phase shifting in the read out direction as explained above, the phase shifting occurring in the read out direction among a plurality of shots included in multi-shot imaging can be corrected with less processing load and in less processing time.

Moreover, in the magnetic resonance imaging apparatus 100 according to the first embodiment, since there is no need to obtain a navigator echo for correction purposes, the scanning time need not be extended for performing correction.

Furthermore, in the magnetic resonance imaging apparatus 100 according to the first embodiment, the pre-correction images 91a to 91c are generated corresponding to a plurality of shots; and correction coefficients are obtained based on the correlation between a single reference image, which is any one image of the pre-correction images 91a to 91c, and each comparison image representing one of the remaining images from among the pre-correction images 91a to 91c. Thus, in the magnetic resonance imaging apparatus 100 according to the first embodiment, a correction coefficient is obtained by comparison of the reference image and a comparison image. For that reason, even if the number of shots increases, there is no increase in the unknown numbers getting calculated in each instance of comparison.

Moreover, in the magnetic resonance imaging apparatus 100 according to the first embodiment, the correction coefficients are obtained in such a way that the coefficient of correlation indicating the correlation of each of a plurality of comparison images with the reference image reaches the maximum value. Hence, in the magnetic resonance imaging apparatus 100 according to the first embodiment, the k-space data corresponding to the other magnetic resonance images are corrected in accordance with the reference image. With that, using simple arithmetic operations, the occurrence of an artifact, which is attributed to the occurrence of phase shifting in the post-correction image, can be reduced in an efficient manner.

Second Embodiment

In the first embodiment, the magnetic resonance imaging apparatus 100 obtains the correction coefficients based on the correlation among a plurality of pre-correction images 91 corresponding to the shots. In a second embodiment, the correction coefficients are obtained based on the pixel values included in ghost regions (i.e., artifact regions) of a magnetic resonance image in which the collection result of each shot is assembled.

The magnetic resonance imaging apparatus 100 according to the second embodiment has an identical configuration to the configuration illustrated in FIG. 1 according to the first embodiment. Moreover, in the magnetic resonance imaging apparatus 100 according to the second embodiment, in an identical manner to the first embodiment, the processing circuit 133 includes the collection function 133a, the generation function 133b, the calculation function 133c, the correction function 133d, the display control function 133e, and the reception function 133f. The collection function 133a has an identical function to the function thereof according to the first embodiment.

The generation function 133b according to the second embodiment generates a single magnetic resonance image using the pre-correction k-space data. That magnetic resonance image represents the pre-correction image according to the second embodiment. Moreover, that magnetic resonance image represents an example of a first-type magnetic resonance image according to the second embodiment. Meanwhile, regarding the method such as SENSE used for image reconstruction, the generation function 133b has an identical function to the function thereof according to the first embodiment.

In the first embodiment, a plurality of magnetic resonance images corresponding to the shots in multi-shot imaging are treated as the pre-correction images. In contrast, in the second embodiment, the generation function 133b implements a method such as SENSE and reconstructs a single pre-correction image from the entire k-space data that is generated from the echo signals collected in the shots. Hence, in the pre-correction image, an artifact occurs due to the phase shifting occurring in the read out direction among the shots.

Moreover, in an identical manner to the first embodiment, the generation function 133b according to the second embodiment generates a magnetic resonance image using the post-correction k-space data. In the following explanation, that magnetic resonance image is called a post-correction image. Moreover, that magnetic resonance image represents an example of a second-type magnetic resonance image according to the second embodiment.

Furthermore, the calculation function 133c according to the second embodiment calculates correction coefficients based on the pixel values included in one or more ghost regions in the pre-correction image.

A ghost region represents such an image region in the pre-correction image in which an artifact has occurred due to the phase shifting occurring in the read out direction among the shots. A ghost region represents an example of an image region according to the second embodiment. In the second embodiment, it is assumed that the ghost regions are manually specified by the user.

Figure 5:
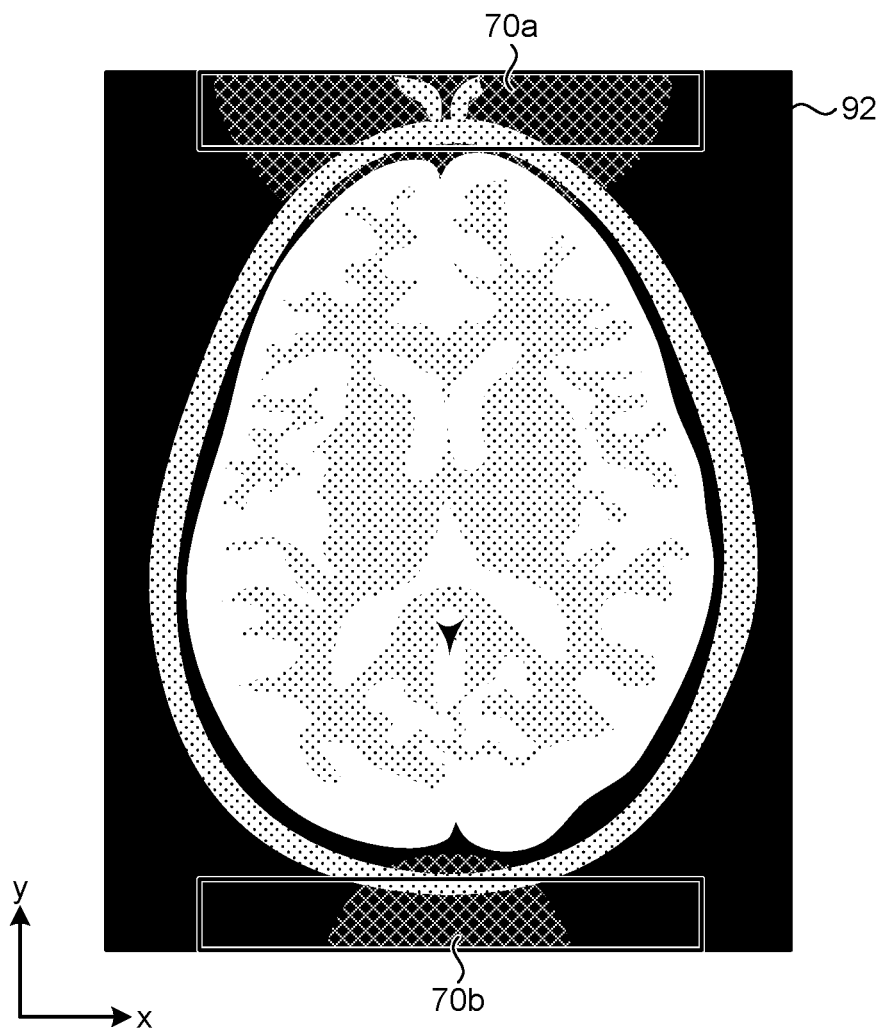
FIG. 5 is a diagram illustrating an example of ghost regions present in a pre-correction image according to a second embodiment.

FIG. 5 is a diagram illustrating an example of ghost regions 70a and 70b present in a pre-correction image 92 according to the second embodiment. As illustrated in FIG. 5, in the ghost regions 70a and 70b, due to the phase shifting occurring in the read out direction among the shots, the tissue of the subject P in white color is visible as an artifact (ghost) at the positions at which the color should be black same as the background. Meanwhile, there is no particular restriction on the number of ghost regions 70a and 70b. In the following explanation, in the case of not particularly distinguishing between the ghost regions 70a and 70b, they are simply referred to as ghost regions 70.

The calculation function 133c according to the second embodiment calculates correction coefficients in such a way that the total value of the pixel values included in the ghost regions 70 in the pre-correction image 92 is minimized. For example, the calculation function 133c solves the optimization problem; and calculates correction coefficients, which are meant for correcting the 0-degree phase shifting and the 1-degree phase shifting, in such a way that the total value of the pixel values included in the ghost regions 70 is minimized.

The pixel values are expressed using, for example, values from "0" to "255". The pixel value "0" represents black and the pixel value "255" represents white. Thus, smaller the pixel value, the closer moves the color to black. That is, when the pixel values included in the ghost regions 70 are minimized, the color of the tissue of the subject P, which is visible as a ghost, moves closer to the black color of the background. As a result, the disturbance in the image decreases.

The calculation function 133c solves the optimization problem only once and obtains, in a simultaneous manner, the correction coefficients meant for correcting the phase shifting among all shots included in multi-shot imaging. For example, in an identical manner to the case illustrated in FIGS. 2 and 3, when the number of shots included in multi-shot imaging is "3", in order to obtain the correction coefficient meant for correcting the 0-degree phase shifting and the 1-degree phase shifting between each pair of shots, the count of unknown numbers becomes equal to "3×2=6". In the second embodiment, with every increase in the number of shots included in multi-shot imaging, there is an increase also in the unknown numbers to be obtained by the calculation function 133c during a single instance of the optimization problem operation. However, regardless of the number of shots included in multi-shot imaging, the optimization problem is solved only once.

The correction function 133d according to the second embodiment corrects the k-space data based on the correction coefficients calculated by the calculation function 133c. For example, using the correction coefficients calculated by the calculation function 133c, the correction function 133d corrects the 0-degree phase shifting and the 1-degree phase shifting in the read out direction with respect to the data obtained by performing inverse Fourier transform in the read out direction of the k-space data; and then performs Fourier transform in the read out direction with respect to the post-correction data so as to obtain the corrected k-space data.

The display control function 133e according to the second embodiment has the functions identical to the functions thereof according to the first embodiment. In addition, the display control function 133e displays, in the display 135, an operation screen for enabling the user to specify the ghost regions 70 in the pre-correction image 92.

The reception function 133f according to the second embodiment has identical functions to the functions thereof according to the first embodiment. In addition, the reception function 133f receives user specification of the ghost regions 70. More particularly, the reception function 133f receives the coordinates indicating the range, in the pre-correction image, of each ghost region 70 specified in the operation screen by the user.

Given below is the explanation of the flow of the correction operation performed in the magnetic resonance imaging apparatus 100 configured as explained above according to the second embodiment.

FIG. 6 is a flowchart for explaining an exemplary flow of the correction operation according to the second embodiment.

The collection operation performed at S21 is identical to the operation performed at S1 according to the first embodiment as explained with reference to FIG. 4.

Then, from the k-space data collected as a result of performing multi-shot imaging, the generation function 133b reconstructs a single pre-correction image 92. In the second embodiment, that operation is called the first image reconstruction operation (S22).

Then, the display control function 133e displays, in the display 135, an operation screen for enabling the user to specify the ghost regions 70 in the pre-correction image 92 (S23).

Subsequently, the reception function 133f receives user specification of the ghost regions 70 (S24). Moreover, the reception function 133f sends the information indicating the coordinates of the received ghost regions 70 to the calculation function 133c.

Then, the calculation function 133c calculates correction coefficients that enable minimizing the total value of the pixel values included in the ghost regions 70 in the pre-correction image 92 (S25).

Subsequently, the correction function 133d corrects the k-space data based on the correction coefficients calculated by the calculation function 133c (S26).

The second image reconstruction operation performed at S27 is identical to the operation performed at S5 according to the first embodiment as explained with reference to FIG. 4. That marks the end of the operations illustrated in the flowchart.

In this way, in the magnetic resonance imaging apparatus 100 according to the second embodiment, a single pre-correction image 92 is generated using the k-space data, and correction coefficients are obtained based on the pixel values included in one or more ghost regions 70 present in the pre-correction image 92. For that reason, in the magnetic resonance imaging apparatus 100 according to the second embodiment, in addition to being able to achieve the effects as achieved in the first embodiment, the correction coefficients enabling reduction in the artifact attributed to phase shifting can be obtained with simple arithmetic operations. For that reason, in the magnetic resonance imaging apparatus 100 according to the second embodiment, correction can be performed with less processing load.

Meanwhile, it is also possible to have a configuration in which the ghost regions 70 are automatically decided. For example, the calculation function 133c can automatically decide on the ghost regions 70 based on the magnitude or the phase dispersion of the echo signals. Alternatively, the calculation function 133c can implement some other image processing method to identify the ranges of artifact occurrence in the pre-correction image 92, and decide the identified ranges as the ghost regions 70. When the ghost regions 70 are automatically decided, the user need not specify the ghost regions 70. Hence, as compared to the method in which the ghost regions 70 are manually decided, it becomes possible to reduce the work load of the user.

Third Embodiment

In a third embodiment, the magnetic resonance imaging apparatus 100 obtains correction coefficients based on an unwrapping error amount of the pre-correction image.

The magnetic resonance imaging apparatus 100 according to the third embodiment has an identical configuration to the configuration illustrated in FIG. 1 according to the first embodiment. Moreover, in the magnetic resonance imaging apparatus 100 according to the third embodiment, the processing circuit 133 includes the collection function 133a, the generation function 133b, the calculation function 133c, the correction function 133d, the display control function 133e, and the reception function 133f. The collection function 133a, the display control function 133e, and the reception function 133*f* have identical functions to the functions thereof according to the first embodiment. The correction function 133*d* has an identical function to the function thereof according to the second embodiment.

In an identical manner to the second embodiment, the generation function 133*b* according to the third embodiment generates a single pre-correction image 92 using the pre-correction k-space data. The pre-correction image 92 represents an example of a first-type magnetic resonance image according to the third embodiment.

The generation function 133*b* calculates the unwrapping error amount occurring at the time of unwrapping the pre-correction image 92 using SENSE.

$$Au = b \qquad (2)$$

$$\text{Err} = \|Au_{sol} - b\| \qquad (3)$$

Herein, Equation (2) is meant to be solved for unwrapping an image according to the SENSE method. Moreover, Equation (3) represents the unwrapping error amount of SENSE to be minimized in the third embodiment.

Regarding Equations (2) and (3), the explanation is given below with reference to FIG. 7. FIG. 7 is a diagram simulatedly illustrating an example of the concept of calculation of the error according to the third embodiment.

In Equation (2), "A" represents an array of maps, such as sensitivity maps 51*a* and 51*b*, indicating the sensitivity of a plurality of coils of the topical RF coil 109. Moreover, "u" represents a vector of the magnetic resonance image to be unwrapped according to the SENSE method. Furthermore, "b" represents a vector of a plurality of coil images 900*a* and 900*b* based on the collected MR data. In the following explanation, in the case of not particularly distinguishing between the sensitivity maps 51*a* and 51*b*, they are simply referred to as sensitivity maps 51. In the following explanation, in the case of not particularly distinguishing between the coil images 51*a* and 51*b*, they are simply referred to as coil images 51.

Since the unwrapping error exists in practice, the generation function 133*b* obtains "Err" (error) by taking the residual norm at both sides in Equation (2) as given in Equation (3). In Equation (3), "$u_{sol}$" represents a vector of the unwrapped magnetic resonance image, and is equivalent to the pre-correction image 92. The generation function 133*b* solves the optimization problem and obtains the correction coefficient in such a way that the error "Err" is minimized.

In FIG. 7, the unwrapping error amounts calculated on a coil-by-coil basis are illustrated as error images 52*a* and 52*b*. Meanwhile, in FIG. 7, the error amount calculated at each point in an image is mapped in the form of an image, and such mapping is displayed. However, in practice, the generation function 133*b* calculates the error amounts as numerical values.

As a result of synthesizing the error images 52*a* and 52*b* of the coils, an error map is obtained. Meanwhile, generation of an error map is not mandatory. In the following explanation, in the case of not particularly distinguishing between the error images 52*a* and 52*b*, they are simply referred to as error images 52.

FIG. 8 is a diagram illustrating an example of a post-correction magnetic resonance image and a post-correction error map according to the third embodiment. The generation function 133*b* performs the unwrapping operation as explained with reference to FIG. 7, and generates the pre-correction image 92 as illustrated in FIG. 8. Moreover, the generation function 133*b* synthesizes the error images 52, each of which corresponds to a coil and is obtained during the unwrapping operation explained with reference to FIG. 7, and generates a pre-correction error map 61. Herein, greater the phase shifting between two shots, the greater is the number of images appearing visible in the pre-correction error map 61. Although there are many reasons for the occurrence of errors, it is an objective of the third embodiment to particularly achieve reduction in the phase shifting occurring in the read out direction among the shots.

Furthermore, in an identical manner to the first and second embodiments, the generation function 133*b* generates a post-correction image 81 using the post-correction k-space data. The post-correction image 81 represents an example of a second-type magnetic resonance image according to the third embodiment.

In the post-correction image 81 generated based on the corrected k-space data, the amount of error during the unwrapping operation is smaller than the amount of error before correction. Hence, when the generation function 133*b* superimposes the error images 52 corresponding to the coils and generates a post-correction error map 62 from the post-corrected k-space data, the amount of images visible in the post-correction error map 62 becomes smaller than in the pre-correction error map 61 as illustrated in FIG. 8. Meanwhile, in FIG. 8, although the pre-correction error map 61 and the post-correction error map 62 are illustrated for the explanation of comparison, the generation function 133*b* need not generate those maps. In the following explanation, simply the term "error map" implies the pre-correction error map 61.

The calculation function 133*c* according to the third embodiment obtains correction coefficients based on the unwrapping error amount that is obtained based on the pre-correction image 92 and based on the sensitivity maps 51 related to the sensitivity of the topical RF coil 109 used in obtaining the k-space data.

More specifically, the calculation function 133*c* solves the optimization problem in such a way that the error "Err" in Equation (3) is minimized, and calculates correction coefficients meant for correcting the 0-degree phase shifting and the 1-degree phase shifting in the read out direction. As a result of using the correction coefficients that enable minimization of the error "Err" in Equation (3), the amount of images visible in the pre-correction error map 61 becomes smaller. In other words, the calculation function 133*c* obtains the correction coefficients in such a way that the amount of images visible in the pre-correction error map 61 becomes smaller.

Given below is the explanation of the flow of the correction operation performed in the magnetic resonance imaging apparatus 100 configured as explained above according to the third embodiment.

FIG. 9 is a flowchart for explaining an exemplary flow of the correction operation according to the third embodiment.

The collection operation performed at S31 is identical to the operation performed at S1 according to the first embodiment as explained with reference to FIG. 4.

Then, the generation function 133*b* performs the first image reconstruction operation and reconstructs a single pre-correction image 92 from the k-space data, which is collected as a result of performing multi-shot imaging, by implementing the SENSE method explained with reference to FIG. 7 (S32).

Subsequently, based on Equation (3), the generation function 133*b* calculates the unwrapping error amount during the operation of obtaining a reconstructed image of the pre-correction image 92 (S33).

Then, the calculation function 133c calculates correction coefficients based on the unwrapping error amount (S34).

Subsequently, the correction function 133d corrects the k-space data based on the correction coefficients calculated by the calculation function 133c (S35).

The second image reconstruction operation performed at S36 is identical to the operation performed at S5 according to the first embodiment as explained with reference to FIG. 4. That marks the end of the operations illustrated in the flowchart.

In this way, in the magnetic resonance imaging apparatus 100 according to the third embodiment, the correction coefficients are obtained based on the unwrapping error amount that is obtained based on the following: the images 900 formed with the k-space data obtained using a plurality of coils; and based on the sensitivity maps 51 indicating the sensitivity of a plurality of coils included in the topical RF coil 109 used in obtaining the images 900. Hence, in the magnetic resonance imaging apparatus 100 according to the third embodiment, the correction coefficients meant for correcting the phase shifting can be obtained using the information that is to be used in unwrapping the magnetic resonance image. Moreover, in the magnetic resonance imaging apparatus 100 according to the third embodiment, the phase shifting among the shots can be corrected without having to identify the ghost regions in which an artifact occurs, and thus the accuracy of the correction operation can be maintained without being swayed by the accuracy of manual specification or automatic specification of the ghost regions. As a result, according to the third embodiment, it becomes possible to provide the magnetic resonance imaging apparatus 100 that is robust in nature and that enables achieving reduction in the work load.

Meanwhile, in the embodiments described above, all operations are performed in the magnetic resonance imaging apparatus 100. However, alternatively, some of the operations can be performed in some other information processing device other than the magnetic resonance imaging apparatus 100. For example, some other information processing device other than the magnetic resonance imaging apparatus 100 can calculate the correction coefficients, and the magnetic resonance imaging apparatus 100 can obtain those correction coefficients. Moreover, some of the functions of the processing circuit 133 of the magnetic resonance imaging apparatus 100 illustrated in FIG. 1 can be implemented using some other information processing device other than the magnetic resonance imaging apparatus 100 or can be implemented using a cloud environment.

Meanwhile, a variety of data handled in the present written description is typically digital data.

Thus, according to at least one embodiment described above, the phase shifting among a plurality of shots included in multi-shot imaging can be corrected with less processing load and in less processing time.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising: processing circuitry configured to
   obtain a correction coefficient, regarding k-space data obtained as a result of performing multi-shot imaging including a plurality of shots, based on a first-type magnetic resonance image generated using the k-space data, the correction coefficient correcting phase shifting occurring in a read out direction among the plurality of shots,
   correct, in k-space, the k-space data based on the correction coefficient, and
   generate a second-type magnetic resonance image using the corrected k-space data.

2. The magnetic resonance imaging apparatus according to claim 1, wherein the processing circuitry is further configured to calculate the correction coefficient based on the first-type magnetic resonance image.

3. The magnetic resonance imaging apparatus according to claim 1, wherein the processing circuitry is further configured to
   generate a plurality of first-type magnetic resonance images respectively corresponding to the plurality of shots, and
   obtain the correction coefficient based on correlation between a reference image, which is one of the plurality of first-type magnetic resonance images, and each of a plurality of comparison images, which are other of the plurality of first-type magnetic resonance images other than the reference image.

4. The magnetic resonance imaging apparatus according to claim 3, wherein
   the plurality of shots at least include a first shot, a second shot, and a third shot, and
   the processing circuitry is further configured to
      obtain, based on a first image representing the reference image corresponding to the first shot from among the plurality of first-type magnetic resonance images and based on a second image representing the comparison image corresponding to the second shot from among the plurality of first-type magnetic resonance images, a first-type correction coefficient with respect to the second image,
      obtain, based on the first image representing the reference image and based on a third image representing the comparison image corresponding to the third shot from among the plurality of first-type magnetic resonance images, a second-type correction coefficient with respect to the third image, and
      correct the k-space data based on the first-type correction coefficient and the second-type correction coefficient.

5. The magnetic resonance imaging apparatus according to claim 3, wherein the processing circuitry is further configured to obtain the correction coefficient in such a way that a coefficient of correlation indicating a correlation of each of the plurality of comparison images with respect to the reference image reaches a maximum value.

6. The magnetic resonance imaging apparatus according to claim 3, wherein
   the k-space data obtained as a result of performing multi-shot imaging represents data obtained using a plurality of coils, and
   the plurality of first-type magnetic resonance images represent a plurality of images reconstructed as a result of performing parallel imaging.

7. The magnetic resonance imaging apparatus according to claim 1, wherein the processing circuitry is further configured to generate a single one of the first-type magnetic resonance image using the k-space data, and obtain the correction coefficient based on pixel values included in one or more image regions in the first-type magnetic resonance image.

8. The magnetic resonance imaging apparatus according to claim 7, wherein the processing circuitry is further configured to determine the one or more image regions either automatically or manually.

9. The magnetic resonance imaging apparatus according to claim 1, wherein the processing circuitry is further configured to generate a single one of the first-type magnetic resonance image using the k-space data, and obtain the correction coefficient based on an unwrapping error amount that is obtained based on the first-type magnetic resonance image and based on a map related to a sensitivity of coils used in obtaining the k-space data.

10. A correction method, comprising:

obtaining a correction coefficient, regarding k-space data obtained as a result of performing multi-shot imaging including a plurality of shots, based on a first-type magnetic resonance image generated using the k-space data, the correction coefficient correcting phase shifting occurring in read out direction among the plurality of shots;

correcting, in k-space, the k-space data based on the correction coefficient; and generating a second-type magnetic resonance image using the corrected k-space data.

11. A memory medium for storing, in a non-transient manner, a computer program that makes a computer execute:

obtaining a correction coefficient, regarding k-space data obtained as a result of performing multi-shot imaging including a plurality of shots, based on a first-type magnetic resonance image generated using the k-space data, the correction coefficient correcting phase shifting occurring in read out direction among the plurality of shots;

correcting, in k-space, the k-space data based on the correction coefficient; and generating a second-type magnetic resonance image using the corrected k-space data.

12. The magnetic resonance imaging apparatus of claim 1, wherein the processing circuitry is configured to perform the multi-shot imaging, which is multi-shot echo planar imaging (EPI).

* * * * *